US012121723B2

(12) United States Patent
Ramos Macias et al.

(10) Patent No.: US 12,121,723 B2
(45) Date of Patent: *Oct. 22, 2024

(54) VESTIBULAR NERVE STIMULATION

(71) Applicant: Universidad de Las Palmas de Gran Canaria, Las Palmas de Gran Canaria (ES)

(72) Inventors: Angel Manuel Ramos Macias, Las Palmas de Gran Canaria (ES); Angel Ramos de Miguel, Las Palmas de Gran Canaria (ES)

(73) Assignee: Universidad de Las Palmas de Gran Canaria, Las Palmas de Gran Canaria (ES)

( * ) Notice: Subject to any disclaimer, the term of this patent is extended or adjusted under 35 U.S.C. 154(b) by 177 days.

This patent is subject to a terminal disclaimer.

(21) Appl. No.: 17/731,801

(22) Filed: Apr. 28, 2022

(65) Prior Publication Data

US 2022/0305263 A1    Sep. 29, 2022

Related U.S. Application Data

(63) Continuation of application No. 16/817,736, filed on Mar. 13, 2020, now Pat. No. 11,351,372.

(30) Foreign Application Priority Data

Jul. 24, 2019  (EP) .................................... 19382632

(51) Int. Cl.
*A61N 1/36*    (2006.01)
*A61N 1/05*    (2006.01)
*A61N 1/372*   (2006.01)

(52) U.S. Cl.
CPC ....... *A61N 1/36036* (2017.08); *A61N 1/0551* (2013.01); *A61N 1/3727* (2013.01)

(58) Field of Classification Search
CPC .............. A61N 1/36036; A61N 1/0551; A61N 1/3727; A61N 1/36034; A61N 1/36057; A61N 1/36067

See application file for complete search history.

(56) References Cited

U.S. PATENT DOCUMENTS 6,314,324 B1    11/2001   Lattner
7,225,028 B2    5/2007    Della Santina et al.
(Continued)

FOREIGN PATENT DOCUMENTS

WO    2010138915 A1    12/2010
WO    2017081335 A1    5/2017

OTHER PUBLICATIONS

Guyot, Jean-Philippe et al., "Adaptation to Steady-State Electrical Stimulation of the Vestibular System in Humans," Annals of Otology, Rhinology & Laryngology vol. 120(3), pp. 143-149, 2011 (7 pages).

(Continued)

*Primary Examiner* — Mark W. Bockelman
(74) *Attorney, Agent, or Firm* — Edell, Shapiro & Finnan, LLC

(57) ABSTRACT

Presented herein are techniques for electrically stimulating a recipient's vestibular nerve in order to mask vestibular noise signals (vestibular noise) generated by the peripheral vestibular system (e.g., prevent erroneous balance information generated by the peripheral vestibular system from being sent to the brain of the recipient). A vestibular nerve stimulator in accordance with embodiments presented herein includes a plurality of electrodes implanted in an inner ear of a recipient at a location that is adjacent to the otolith organs of the inner ear. The vestibular nerve stimulator is configured to generate one or more continuous pulse trains (Continued)

and to deliver the one or more continuous pulse trains to the inferior branch of the recipient's vestibular nerve.

11 Claims, 14 Drawing Sheets

(56) References Cited

U.S. PATENT DOCUMENTS

| | | | |
|---|---|---|---|
| 7,933,654 | B2 | 4/2011 | Merfeld |
| 8,355,788 | B2 | 1/2013 | Mechlenburg |
| 8,751,012 | B2 | 6/2014 | Jäger |
| 9,089,692 | B2 | 7/2015 | Risi et al. |
| 9,242,094 | B2 | 1/2016 | Della Santina |
| 9,339,649 | B2 | 5/2016 | Cushing |
| 11,351,372 | B2 * | 6/2022 | Ramos Macias .. A61N 1/36067 |
| 2002/0072781 | A1 | 6/2002 | Attner |
| 2004/0199214 | A1 | 10/2004 | Merfeld |
| 2012/0226187 | A1 | 9/2012 | Bierer |
| 2013/0066424 | A1 | 3/2013 | Hessler |
| 2013/0184788 | A1 | 7/2013 | Jaeger |
| 2014/0228954 | A1 | 8/2014 | Hessler |
| 2015/0039057 | A1 | 2/2015 | Della Santina |
| 2015/0066126 | A1 | 3/2015 | Marx |

OTHER PUBLICATIONS

Nie, Kaibao et al., "Characterization of the Electrically Evoked Compound Action Potential of the Vestibular Nerve," Otology & Neurotology, vol. 32, pp. 88-97, 2010 (9 pages).

Ramos de Miguel, Angel et al., "Vestibular Response to Electrical Stimulation of the Otolith Organs. Implications in the Development of a Vestibular Implant for the Improvement of the Sensation of Gravitoinertial Accelerations," The Journal of International Advanced Otology, vol. 13(2), pp. 154-161, 2017 (8 pages).

Thompson, Lara et al., "Responses evoked by a vestibular implant providing chronic stimulation," Journal of Vestibular Research, vol. 22, pp. 11-15, 2012 (6 pages).

Extended European Search Report received in European application No. 20164292.3, dated Nov. 26, 2020 (8 pages).

Extended European Search Report received in European Application No. 24152868.6, dated Mar. 20, 2024 (7 pages).

* cited by examiner

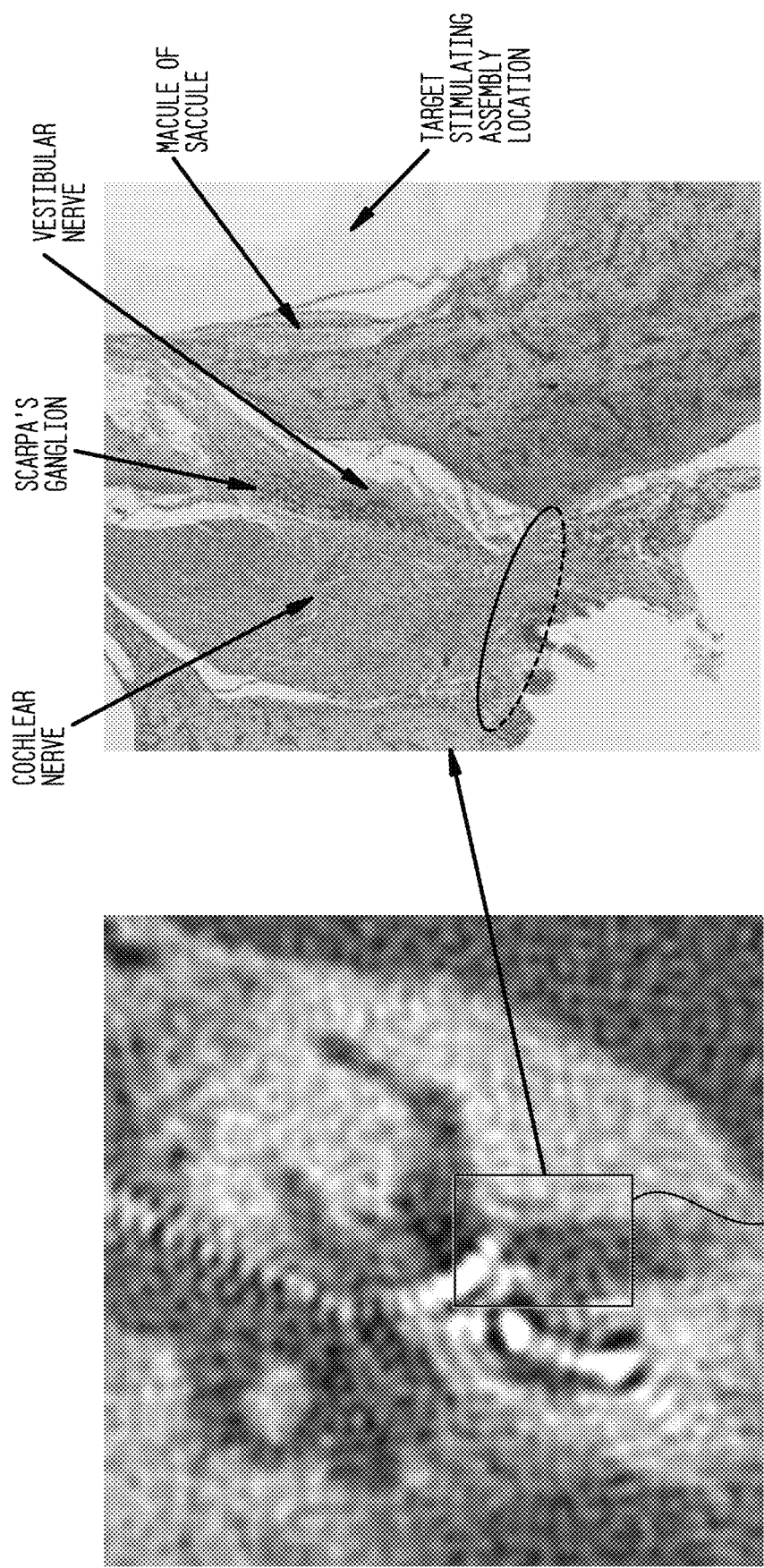

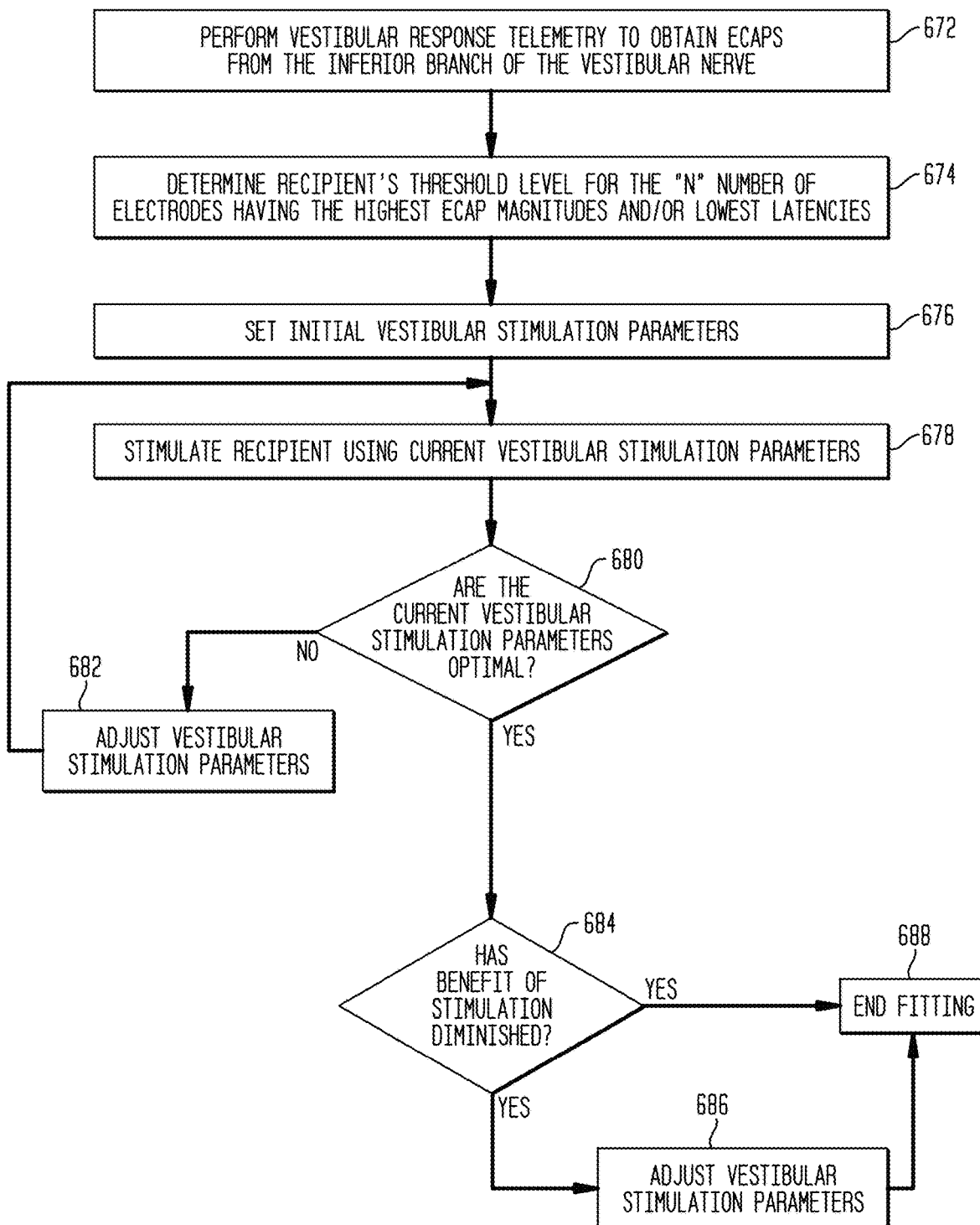

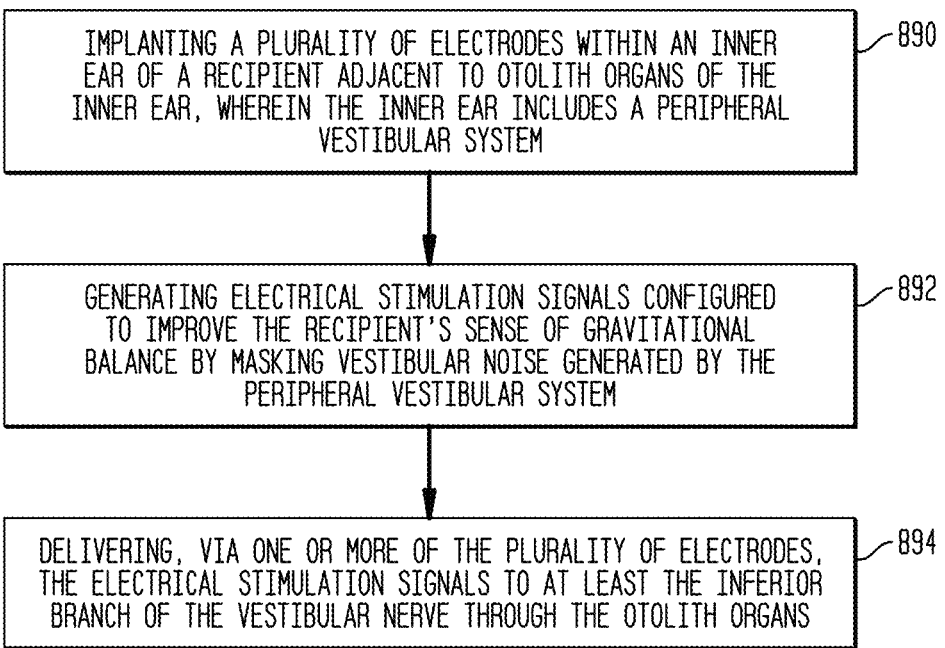

VESTIBULAR NERVE STIMULATION

CROSS-REFERENCE TO RELATED APPLICATIONS

This application is a continuation application of U.S. application Ser. No. 16/817,736, filed on Mar. 13, 2020, which claims priority to European Patent Application No. 19 382 632, filed on Jul. 24, 2019, and entitled "Vestibular Nerve Stimulation," the content of which is hereby incorporated by reference herein.

FIELD OF THE INVENTION

The present invention generally relates to stimulation of a recipient's vestibular nerve.

STATEMENT OF FUNDING

The project leading to this application has received funding from the European Union's Horizon 2020 research and innovation programme under grant agreement No 801127.

RELATED ART

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect, a method is provided. The method comprises: implanting a plurality of electrodes within an inner ear of a recipient adjacent to otolith organs of the inner ear and the internal auditory canal, wherein the inner ear includes a peripheral vestibular system; generating electrical stimulation signals configured to improve the recipient's sense of gravitational balance by masking vestibular noise generated by the peripheral vestibular system; and delivering, via one or more of the plurality of electrodes, the electrical stimulation signals to at least the inferior branch of the vestibular nerve through the otolith organs.

In another aspect, a vestibular nerve stimulator is provided. The vestibular nerve stimulator comprises: a stimulating assembly comprising a plurality of electrodes configured to be implanted in an inner ear of a recipient adjacent to the saccule of the inner ear; and a stimulator unit configured to generate and deliver one or more continuous electrical pulse trains to the to the inferior branch of the vestibular nerve of the recipient via one or more of the plurality of electrodes, wherein the one or more continuous electrical pulse trains are configured to suppress, mostly in the inferior branch of the vestibular nerve and partially in superior branch, erroneous balance information generated by the peripheral vestibular system of the inner ear that would otherwise be sent to the brain of the recipient by the vestibular nerve.

BRIEF DESCRIPTION OF THE DRAWINGS

Embodiments of the present invention are described herein in conjunction with the accompanying drawings, in which:

FIGS. 3B, 3C, 3D, 3E, 3F, and 3G are annotated computerized tomography (CT) scans illustrating implantation of a stimulating assembly of a vestibular nerve stimulator into a recipient, in accordance with certain embodiments presented herein:

FIG. 3H is a medical image illustrating nerve cells adjacent to an implanted location of a stimulating assembly of a vestibular nerve stimulator, in accordance with certain embodiments presented herein:

FIG. 5A is a graph illustrating an example electrically evoked compound action potential (ECAP) that may be obtained from a recipient's vestibular nerve using Vestibular Response Telemetry, in accordance with certain embodiments presented herein:

FIG. 6 is a flowchart of a method, in accordance with certain embodiments presented herein:

FIG. 8 is a flowchart of another method, in accordance with certain embodiments presented herein.

DETAILED DESCRIPTION

Presented herein are techniques for electrically stimulating a recipient's vestibular nerve in order to mask vestibular noise signals (vestibular noise) generated by the peripheral vestibular system (e.g., prevent erroneous balance information generated by the peripheral vestibular system from being sent to the brain of the recipient). A vestibular nerve stimulator in accordance with embodiments presented herein includes a plurality of electrodes implanted in an inner ear of a recipient at a location that is adjacent to the otolith organs of the inner ear. The vestibular nerve stimulator is configured to generate one or more continuous pulse trains and to deliver the one or more continuous pulse trains to the inferior branch of the recipient's vestibular nerve.

Unlike prior art systems, vestibular nerve stimulators in accordance with certain embodiments presented herein do not need to rely on inputs from body motion sensors to deliver an effective treatment (e.g., the one or more continuous pulse trains may be generated independent of any sensor inputs relating to motion of the head of the recipient, angular accelerations of the head, etc.). Instead, and as described further below, the one or more continuous pulse trains are delivered so that the recipient continually experiences a sense of balance for periods of time, such as throughout the entire day, while the recipient is in an upright position, while performing certain activities, etc. To ensure that the recipient continually experiences a sense of balance, electrical stimulation signals in accordance with embodiments presented herein are generally delivered for extended periods of time to account for the recipient's disbalance in some manner, while taking into account recipient-specific characteristics and the residual effects of the stimulation. In certain examples, the electrical stimulation signals are delivered to the recipient continually constantly through the day (e.g., continually deliver stimulation signals for 8 hours, 12 hours, 14 hours, etc.). In other examples, a vestibular nerve stimulator in accordance with embodiments presented herein could deliver stimulation signals to the vestibular nerve at a specific duty cycle that ensures that the recipient continually experiences a sense of balance.

Figure 1A:
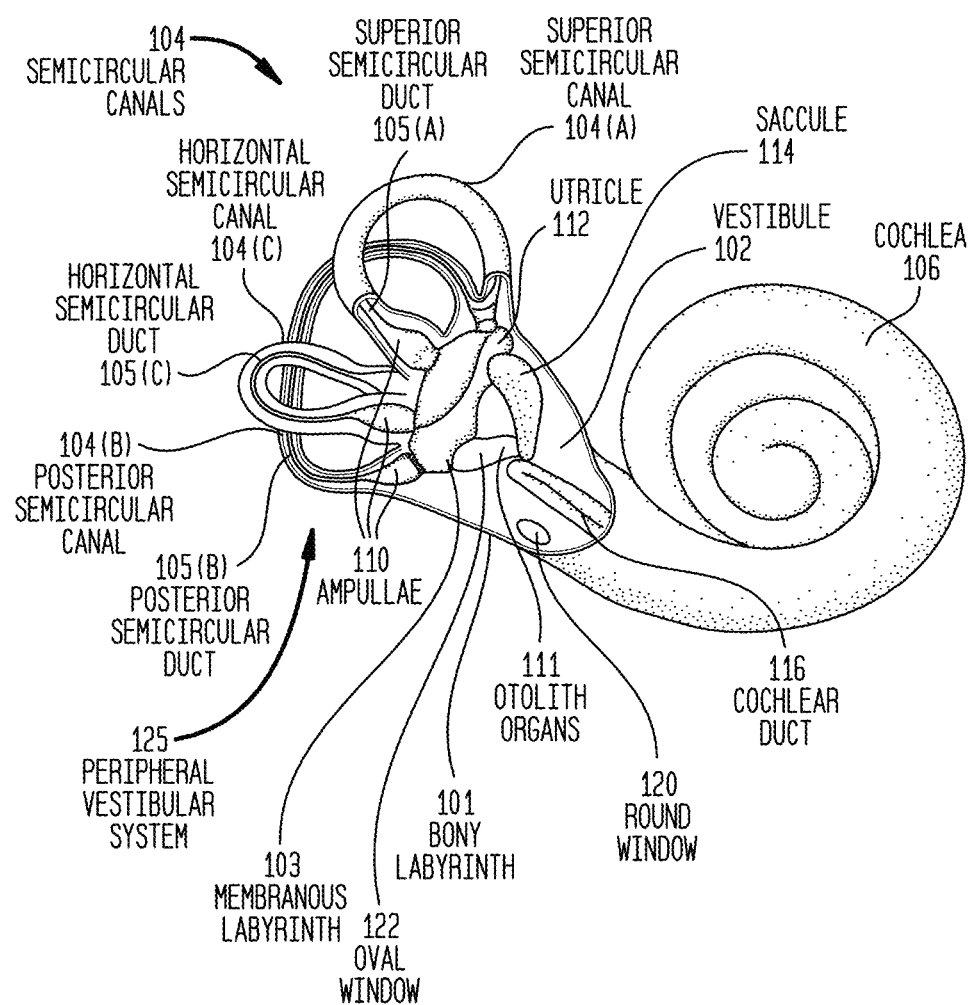
FIG. 1A is a schematic, partial cross-sectional view illustrating anatomical structures of the human inner ear.
Figure 1B:
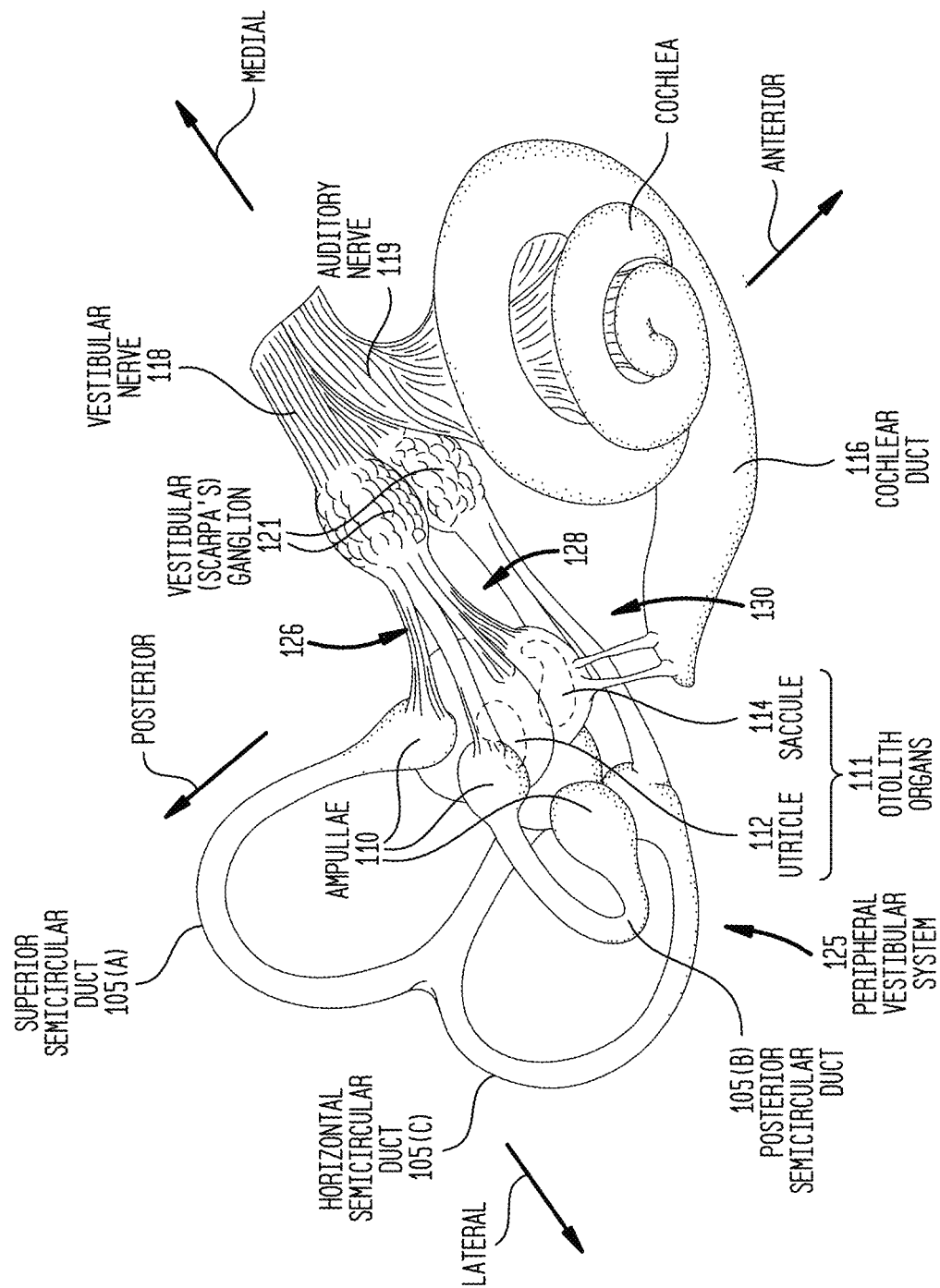
FIG. 1B is a perspective view illustrating further details of a portion of the human inner ear of FIG. 1A.

Before describing details of the vestibular nerve stimulation techniques presented herein, relevant aspects of an example human inner ear are first described below with reference to FIGS. 1A and 1B. In particular, shown in FIG. 1A is the bony labyrinth 101, which is the bony outer wall of an inner ear 100. The bony labyrinth 101 includes three sections/parts, referred to as the vestibule 102, which includes the Otolith organs 111, the semicircular canals 104, and the cochlea 106. The vestibule 102, the semicircular canals 104, and the cochlea 106 are cavities that are internally lined with periosteum and that contain a fluid known as perilymph. For ease of illustration, a portion of the bony labyrinth 101 forming the vestibule 102 has been omitted from FIG. 1A, while the entire bony labyrinth 101 has been omitted from FIG. 1B.

Within the bony labyrinth 101 is the membranous labyrinth 103, which consists of the semicircular ducts 105, the otolith organs 111 (i.e., the utricle 112 and the saccule 114), and the cochlear duct 116. The membranous labyrinth 103 is filled with a fluid known as endolymph, and is surrounded by the perilymph of the bony labyrinth 101. The membranous labyrinth 103 is also suspended from the bony labyrinth 101 by fine connective tissue strands.

As shown, the bony labyrinth 101 includes three (3) semicircular canals 104, referred to as the superior or anterior semicircular canal 104(A), the posterior semicircular canal 104(B), and the horizontal or lateral semicircular canal 104(C). Within the superior semicircular canal 104(A) is the superior semicircular duct 105(B), within the posterior semicircular canal 104(B) is the posterior semicircular duct 105(B), and within the horizontal semicircular canal 104(C) is the horizontal semicircular duct 105(C). The semicircular ducts 105 are situated superoposterior to the vestibule 102 and each have a swelling at one end, known as an ampulla 110 (i.e., three ampullae are shown in FIGS. 1A and 1B, one for each duct 105).

The semicircular ducts 105(A), 105(B), and 105(C) are half-circular, interconnected tubes that are aligned approximately orthogonally to one another (i.e., at right angles to each other) so that they measure motions in all three planes. Specifically, lateral duct 105(C) is aligned roughly horizontally in the head, while the superior 105(A) and posterior ducts 105(B) are aligned roughly at a 45 degree angle to a vertical through the center of the individual's head. The semicircular ducts 105(A), 105(B), and 105(C) are each maximally sensitive to angular accelerations (head rotations) that lie in the plane of the duct. The result of this arrangement is that three semicircular ducts 105(A), 105(B), and 105(C) can uniquely specify the direction and amplitude of any arbitrary head rotation. That is, upon movement of the head, the flow of endolymph within the ducts 105 changes speed and/or direction. Sensory receptors in the ampullae 110 detect these changes, and send signals to the brain via the vestibular nerve 118 (FIG. 1B), allowing for the processing of balance.

As noted, the membranous labyrinth 103 also includes the utricle 112 and the saccule 114, which are collectively referred to as the otolith organs 111. The utricle 112 and the saccule 114 are two membranous sacs located in the vestibule 102, which detect movement or acceleration of the head in the horizontal and vertical planes, respectively (i.e., linear accelerations). The utricle 112 is the larger of the two, receiving the three semi-circular ducts 105. The saccule 114 is globular in shape and receives the cochlear duct 116.

The utricle 112 and the saccule 114 each contain a macula, which is an organ consisting of a patch of hair cells covered by a gelatinous membrane containing particles of calcium carbonate, called otoliths. Motions of the head cause the otoliths organs 111 to pull on these hair cells, stimulating the vestibular nerve 118, which allow the individual to perceive linear acceleration, both horizontally and vertically, and gravity control (i.e., gravitoinertial information).

The vestibular nerve 118 is one of the two branches of the vestibulocochlear nerve (the other being the auditory nerve 119), which functions to relay/transmit sensory information transmitted by the vestibular hair cells located in the two otolith organs (i.e., the utricle 112 and the saccule 114) and the three semicircular ducts 105 via the vestibular (Scarpa's) ganglion 121. Again, as noted, information from the otolith organs 111 reflects gravity and linear accelerations of the head, while information from the semicircular ducts 105 reflects rotational movement of the head.

The peripheral vestibular nerve fibers are generally divided into three branches. First, the superior vestibular nerve branch 126 passes through the foramina in the area vestibularis superior and ends in the utricle 112 and in the ampullae 110 of the superior and horizontal semicircular ducts 105(A) and 105(C), respectively. Second, the inferior vestibular nerve branch 128 traverse the foramina in the area vestibularis inferior and ends in the saccule 114. Third, posterior vestibular nerve branch 130 runs through the foramen singulare and supplies the ampulla 110 of the posterior semicircular duct 105(B), in more than 50% of the cases is part of the inferior branch.

Also shown in FIG. 1A is the round window 120 and the oval window 122. The round window 120 and oval window 122 are the two openings from the middle ear (not shown) into the inner ear 100. The round window 120 is situated inferior to (below) and posterior to (behind) the oval window 122, from which it is separated by the promontory (rounded elevation). The oval window 122 is sealed by a membrane (oval window membrane) and leads from the middle ear to the vestibule of the inner ear 100. Vibrations that contact the tympanic membrane (ear drum) in the outer ear (not shown) travel through the three ossicles (i.e., malleus, incus, and stapes) of the middle ear and into the inner ear 100 via the oval window 122. That is, the oval window 122 is the intersection of the middle ear with the inner ear 100 and is directly contacted by the stapes. The round window 120 is also sealed by a membrane (round window membrane), which vibrates with opposite phase to vibrations entering the inner ear 100 through the oval window 122. The round window 120 allows fluid in the cochlea 106 to move.

As noted above, the inner ear 100 includes the semicircular ducts 105, the utricle 112, and the saccule 114, which collectively form what is referred to as the "peripheral vestibular apparatus" or the "peripheral vestibular system" 125. As noted, in an individual with a fully functional peripheral vestibular system 125, the vestibular system is able to sense head tilt and rotation during movement, which in turn helps the individual maintain balance, stabilize vision, etc. However, certain individuals may suffer from a balance disorder with complete or partial loss of vestibular system function/sensation in one or both ears. In general, a balance disorder is a condition in which an individual lacks the ability to control and/or maintain a proper (balanced) body position in a comfortable manner (i.e., the recipient experiences some sensation(s) of disbalance). Disbalance, sometimes referred to herein as balance problems, can manifest in a number of different manners, such as feelings of unsteadiness or dizziness, a feeling of movement, spinning, or floating, even though standing still or lying down, falling, difficulty walking in darkness without falling, blurred or unsteady vision, inability to stand or walk unaided, etc. Balance disorders can be caused by certain health conditions, medications, aging, infections, head injuries, problems in the inner ear, problems with brain or the heart, problems with blood circulation, etc.

In general, a "balance prosthesis" or "balance implant" is a medical device that is configured to assist recipients (i.e., persons in which a balance prosthesis is implanted) that suffer from balance disorders. Although different balance prosthesis have been proposed to treat different types/causes of balance disorders, much conventional research has focused on devices, sometimes referred to as vestibular implants, that stimulate the ampullas 110 of semicircular ducts 105. Most conventional vestibular implants devices attempt to measure recipient head movement with a sensor and then convert the sensed head movement into electrical stimulation signals. The electrical stimulation signals are delivered to the recipient's semicircular ducts via one or more electrodes in or near the semicircular ducts. That is, vestibular implant research has mostly focused on the detection of angular velocity of the cephalic movements through sensors (e.g., gyroscopes) and stimulate the three-ampulla crests of the semicircular canals in order to improve the vestibular ocular reflex. However, there are recipient head movements corresponding to vertical and horizontal acceleration that are related to the sensation of gravitoinertial accelerations which are not addressed by such conventional vestibular implants (i.e., such movements are detected by the macules of the saccule and the utricle, which are not be stimulated with the electrodes implanted in or near the semicircular canals).

Another problem with conventional vestibular implants is that they only operate in a reactive manner to treat an acute onset of a balance issue. For example, most conventional vestibular implants only stimulate the semicircular ducts after the onset of some disbalance symptoms, where the disbalance symptoms are usually detected through one or more sensors or by the recipient (i.e., conventional vestibular implants only operate to treat a balance problem after it starts to occur).

Presented herein are techniques for treating balance disorders in a proactive, rather than reactive. In particular, presented herein is a new type of balance prosthesis referred to as a "vestibular nerve stimulator." As used herein, a vestibular nerve stimulator is a medical device that is configured to electrically stimulate (i.e., deliver electrical stimulation signals (current signals) to) a recipient's vestibular nerve. That is, a vestibular nerve stimulator generates electrical stimulation signals that are specifically configured to evoke a response in one or more segments of the vestibular nerve, such as the vestibular ganglion, inferior branch of the vestibular nerve, and/or the superior branch of the vestibular nerve. In contrast to vestibular nerve stimulators in accordance with embodiments presented, conventional vestibular implants do not generate electrical stimulation signals that are specifically configured to evoke a response in one or more segments of the vestibular nerve. Instead, as noted above, conventional vestibular implants only generate stimulation signals configured to stimulate one or more parts of the peripheral vestibular system, such as the ampulla associated with the semicircular ducts.

In accordance with embodiments presented herein, a vestibular nerve stimulator includes a stimulating assembly, which comprises a plurality of electrodes. The stimulating assembly is implanted into the inner ear of the recipient adjacent to the otolith organs, via, for example, the recipient's oval window, through an anterior opening such as an estapedotomy, etc. Once implanted, the vestibular nerve stimulator is configured to electrically stimulate the vestibular ganglion in a manner that improve the recipient's sense of gravitational balance by masking vestibular noise signals (vestibular noise) generated by the peripheral vestibular system. As used herein. "vestibular noise signals" or "vestibular noise" refers to erroneous gravitoinertial (gravito-inertial) acceleration information generated by the peripheral vestibular system, namely the otolith organs. As a result, vestibular nerve stimulators in accordance with embodiments presented herein can proactively prevent a recipient from experiencing the manifestation of chronic balance disorders (e.g., prevent the recipient from feeling disbalanced). The electrically stimulation delivered to the inferior vestibular nerve branch may "suppress" vestibular noise signals and restore stable function to the non-functional system with asynchronic neural activity.

Figure 2A:
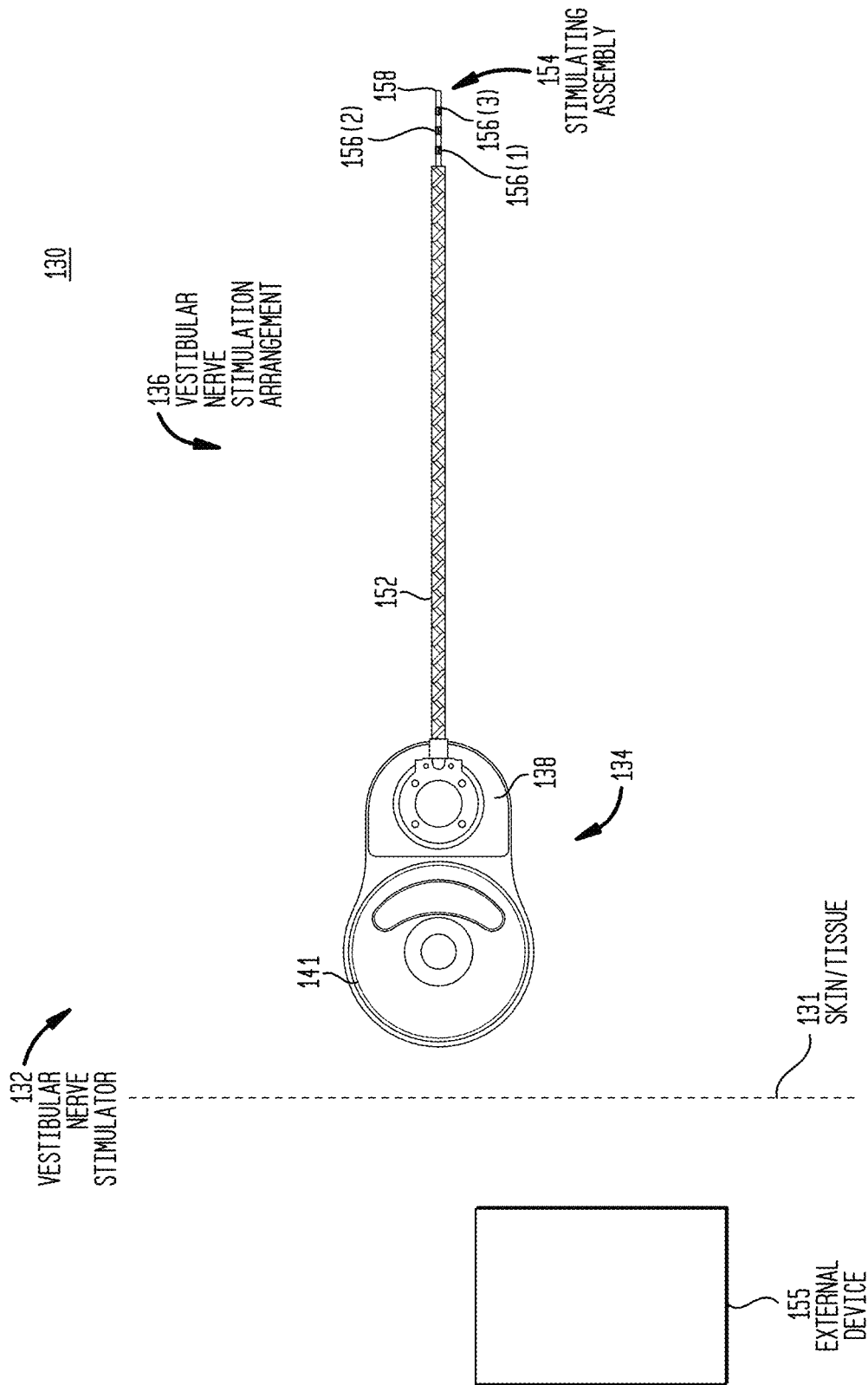
FIG. 2A is a schematic diagram illustrating a vestibular stimulation system, in accordance with certain embodiments presented herein.
Figure 2B:
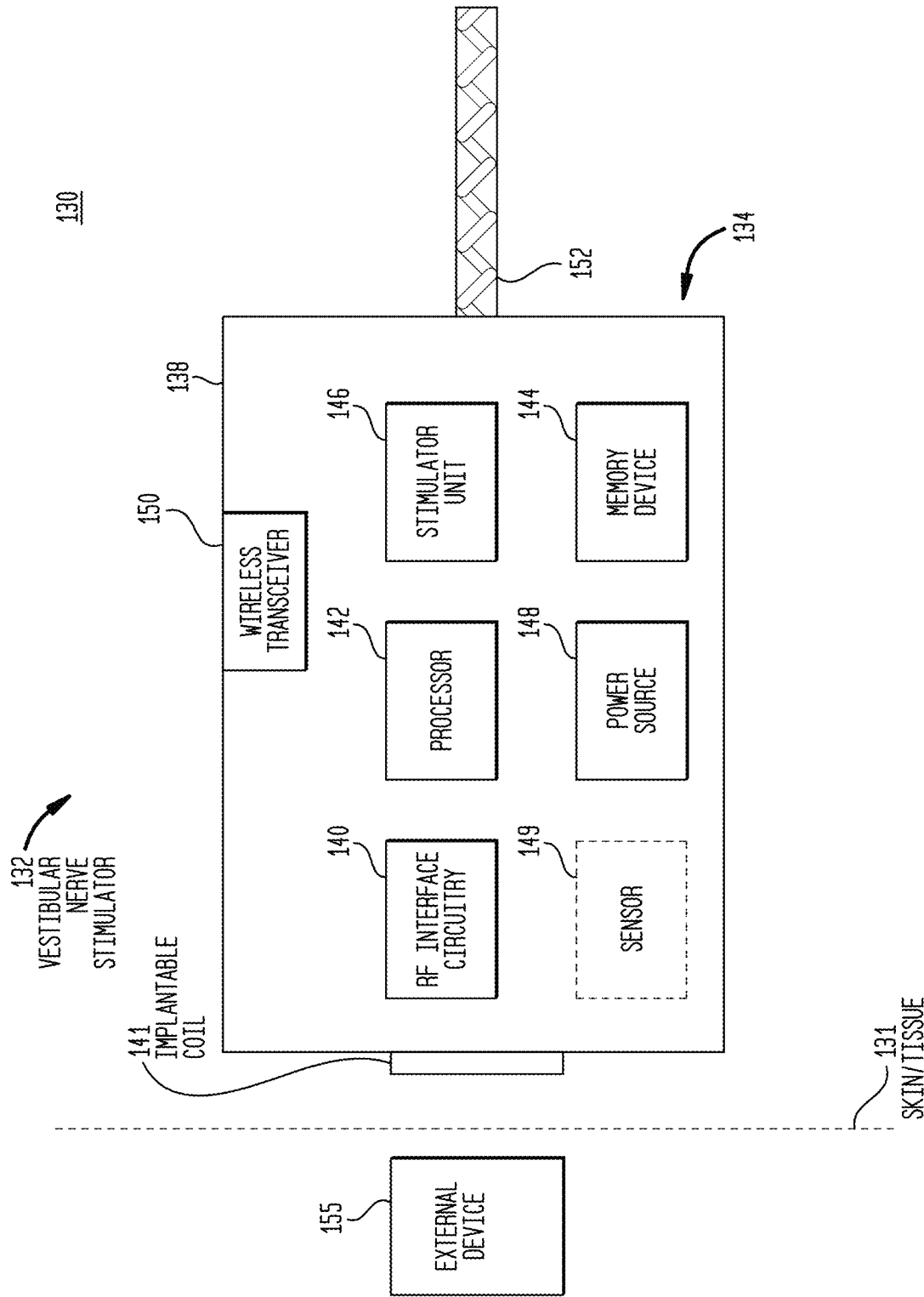
FIG. 2B is a simplified block diagram of the vestibular stimulation system of FIG. 2A, in accordance with certain embodiments presented herein.

FIGS. 2A and 2B illustrate further details of one example vestibular nerve stimulation system in accordance with embodiments presented herein. More specifically, shown in FIG. 2A is a perspective view of a vestibular nerve stimulation system 130, which includes a vestibular nerve stimulator 132. FIG. 2B is a block diagram of the vestibular nerve stimulator 132. For ease of description. FIGS. 2A and 2B will be described together. Also for ease of illustration, certain components of the vestibular nerve stimulator 132 are described with reference to the inner ear 100 of FIGS. 1A and 1B.

As shown, the vestibular nerve stimulator 120 comprises an implant body (main module) 134 and a vestibular nerve stimulation arrangement 136, both of which are implantable within a recipient (i.e., implanted under the skin/tissue 131 of a recipient). The implant body 134 generally comprises a hermetically-sealed housing 138 in which Radio-Frequency (RF) interface circuitry 140, at least one processor 142, a memory device (memory) 144, a stimulator unit 146, a rechargeable power source 148, and a wireless transmitter/receiver (transceiver) 150 are disposed. The implant body 134 also includes an internal/implantable coil 141 that is generally external to the housing 138, but which is connected to the RF interface circuitry 140 via a hermetic feedthrough (not shown in FIG. 2B).

The processor 142 may be formed by one or more processors (e.g., one or more Digital Signal Processors (DSPs), one or more uC cores, etc.), firmware, software, etc. arranged to perform operations described herein. That is, the processor 142 may be implemented as firmware elements, partially or fully implemented with digital logic gates in one or more application-specific integrated circuits (ASICs), partially in software, etc. In general, the processor 142 may instruct the stimulator unit 146 to generate and deliver electrical stimulation signals to the recipient's vestibular nerve. The processor 142 may also perform other operations, include data logging, battery monitoring and low-battery alarm, etc. The stimulator unit 146 may include, for example, one or more current sources, switches, etc., that collectively operate to generate and deliver the electrical stimulation signals to the recipient via the vestibular stimulation arrangement 124.

As shown in FIG. 2A, the vestibular stimulation arrangement 124 comprises a lead 152 and a vestibular nerve stimulating (electrode) assembly 154. The stimulating assembly 154 comprises a plurality of electrodes 156 disposed in a carrier member 158 (e.g., a flexible silicone body). In this specific example, the stimulating assembly 154 comprises three (3) electrodes, referred to as electrodes 156(1), 156(2), and 156(3). As described further below, the electrodes 156(1), 156(2), and 156(3) function as an electrical interface to the recipient's vestibular nerve. It is to be appreciated that this specific embodiment with three electrodes is merely illustrative and that the techniques presented herein may be used with stimulating assemblies having different numbers of electrodes, stimulating assemblies having different lengths, etc.

As described elsewhere herein, the stimulating assembly 154 is configured such that a surgeon can implant the stimulating assembly adjacent the otolith organs 111 of the peripheral vestibular system 125 via, for example, the recipient's oval window 122. That is, the stimulating assembly 154 has sufficient stiffness and dynamics such that the stimulating assembly can be inserted through the oval window 122 and placed reliably within the bony labyrinth 101 adjacent the otolith organs 111 (e.g., sufficient stiffness to insert the stimulating assembly to the desired depth between the bony labyrinth 101 and the membranous labyrinth 103). In certain examples, the stimulating assembly 154 is configured to be placed adjacent the saccule 114.

In general, the stimulating assembly 154 has a stiffness allowing a single stroke atraumatic insertion to the required depth in the bone labyrinth 101. However, the stimulating assembly 154 may also have sufficient flexibility to deflect and avoid damage to the delicate anatomical structures of the inner ear 100.

The lead 152 has a configuration (e.g., length, flexibility, etc.) that allows for ease of surgical placement of the stimulating assembly 154 and that improves lead reliability (impact, fatigue, stress, etc.). In certain examples, the stimulating assembly 154 includes a removable or deformable stiffening member allowing placement of the stimulating assembly within the bony labyrinth 101.

As noted above, the vestibular nerve stimulator 132 comprises RF interface circuitry 140 and a rechargeable power source 148 (e.g., one or more rechargeable batteries). The power source 148 is recharged using power received from an external device 155 via the RF interface circuitry 140. That is, although not shown in FIG. 2B, the external device 154 comprises an external coil configured to be inductively coupled with the implantable coil 141. When inductively coupled, the external coil and the implantable coil 141 form a closely-coupled wireless link by which power is transferred from a power source of the external device through the skin/tissue 131 of the recipient. In certain examples, the closely-coupled wireless link is a radio frequency (RF) link. However, various other types of energy transfer, such as infrared (IR), electromagnetic, capacitive and inductive transfer, may be used to transfer the power and/or data from the external device to the vestibular nerve stimulator 132.

As described elsewhere herein, vestibular nerve stimulators in accordance with certain embodiments presented herein do not need to rely on inputs from body motion sensors to deliver an effective treatment (e.g., the one or more continuous pulse trains may be generated independent of any sensor inputs relating to motion of the head of the recipient, angular accelerations of the head, etc.). However, also shown in FIG. 2B is an optional sensor 149 which may be used in certain embodiments. The sensor 149 may be a sensor configured to, for example, to sense gravitoinertial accelerations (e.g., measure linear accelerations), a sensor to detect the recipient's posture, etc.

It is to be appreciated that the specific arrangement for vestibular nerve stimulator 132, and more generally the system 130, shown in FIGS. 2A and 2B is merely illustrative. As such, it is to be appreciated that vestibular nerve stimulators and associated systems may have a number of different arrangements in which, for example, the various functional components shown in FIG. 2B are implemented at one or a plurality of separate components, devices, etc.

Provided below are further details relating to: (1) the implantation of a stimulating vestibular nerve assembly of a vestibular nerve stimulator into a recipient. (2) the "fitting" or "programming" of a vestibular nerve stimulator for a recipient, and (3) the operation of a vestibular nerve stimulator to electrically stimulate to a recipient's inferior vestibular nerve.

As noted above, a stimulating assembly in accordance with embodiments presented herein is configured to be implanted adjacent the otolith organs, in particular the saccule, of the recipient's peripheral vestibular system via the recipient's oval window. From a surgical perspective, the saccule is the most interiorly (distally) accessible point of the recipient's peripheral vestibular system and is positioned immediately adjacent to the inferior branch of the vestibular nerve and near the vestibular ganglion. As such, implantation of the stimulating assembly adjacent to the saccule also places the electrodes of the stimulating assembly adjacent to the inferior branch of the vestibular nerve and the vestibular ganglion. Therefore, and as described elsewhere herein, the positioning of the stimulating assembly adjacent to the saccule allows electrical stimulation of the inferior branch of the vestibular nerve and the vestibular ganglion that is either direct stimulation, or indirect stimulation through only the saccule. That is, the electrical stimulation (current) signals pass directly from the electrodes to the inferior branch of the vestibular nerve and/or to the vestibular ganglion, or from the electrodes to the inferior branch of the vestibular nerve and/or to the vestibular ganglion via the saccule. The positioning of the stimulating assembly adjacent to the saccule accordingly may ensure that the inferior branch of the vestibular nerve and the vestibular ganglion can be stimulated without having the stimulation pass through utricle (which if stimulated could potentially induce problems for the recipient).

Figure 3A:
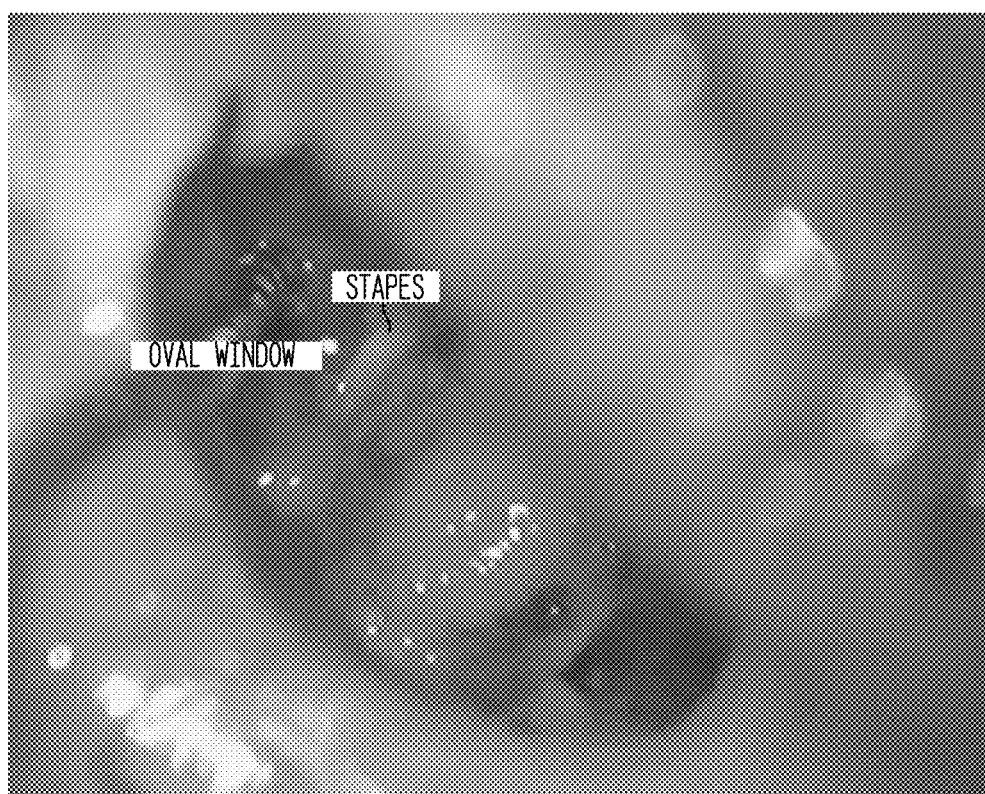
FIG. 3A is an image illustrating implantation of a stimulating assembly of a vestibular nerve stimulator into a recipient, in accordance with certain embodiments presented herein.
Figure 3C:
Figure 3B:
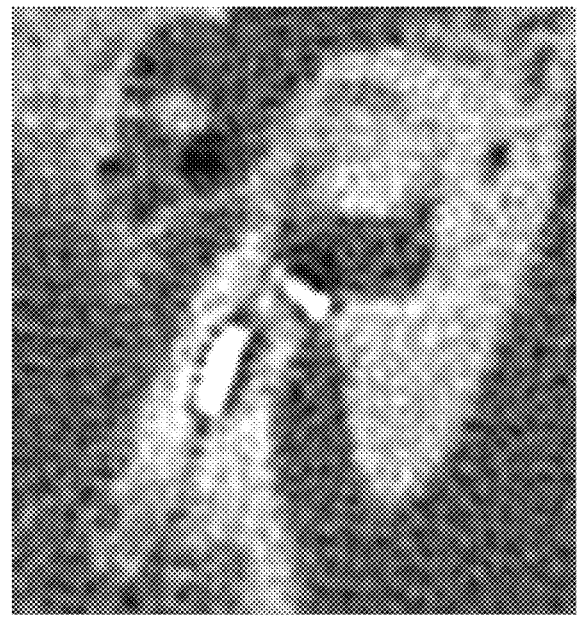
Figure 3F:
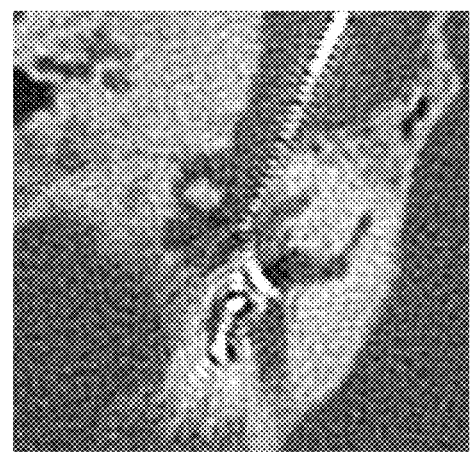
Figure 3E:
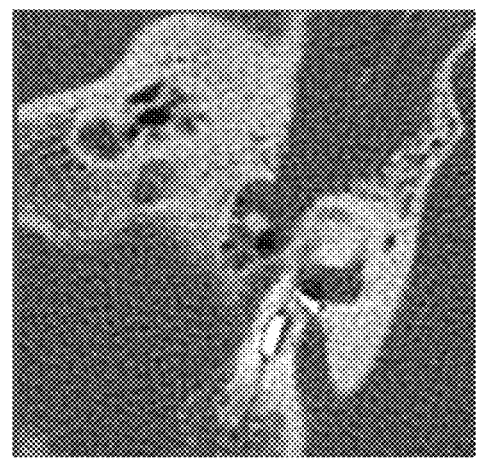
Figure 3D:
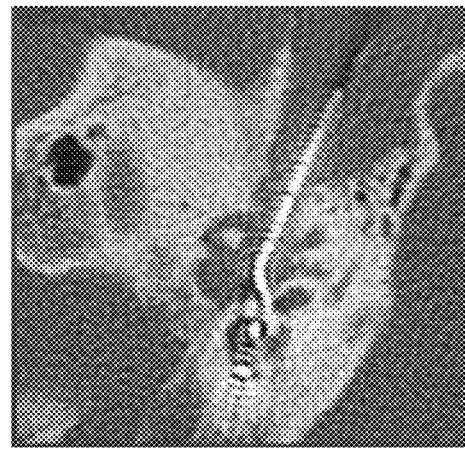

FIG. 3A is an image illustrating implantation of a stimulating assembly of a vestibular nerve stimulator into a recipient, in accordance with embodiments presented herein. More specifically, FIG. 3A illustrates insertion of a stimulating assembly via a recipient's oval window: FIGS. 3B-3G are computerized tomography (CT) scans illustrating implantation of a stimulating assembly into an inner ear of a recipient, in accordance with embodiments presented herein. As shown by FIG. 3G, and accompanying annotated medical image FIG. 3H, the stimulating assembly of a vestibular nerve stimulator in accordance with embodiments presented herein is closely positioned to the vestibular ganglion (Scarpa's ganglion) of the inferior vestibular nerve.

Figure 4:
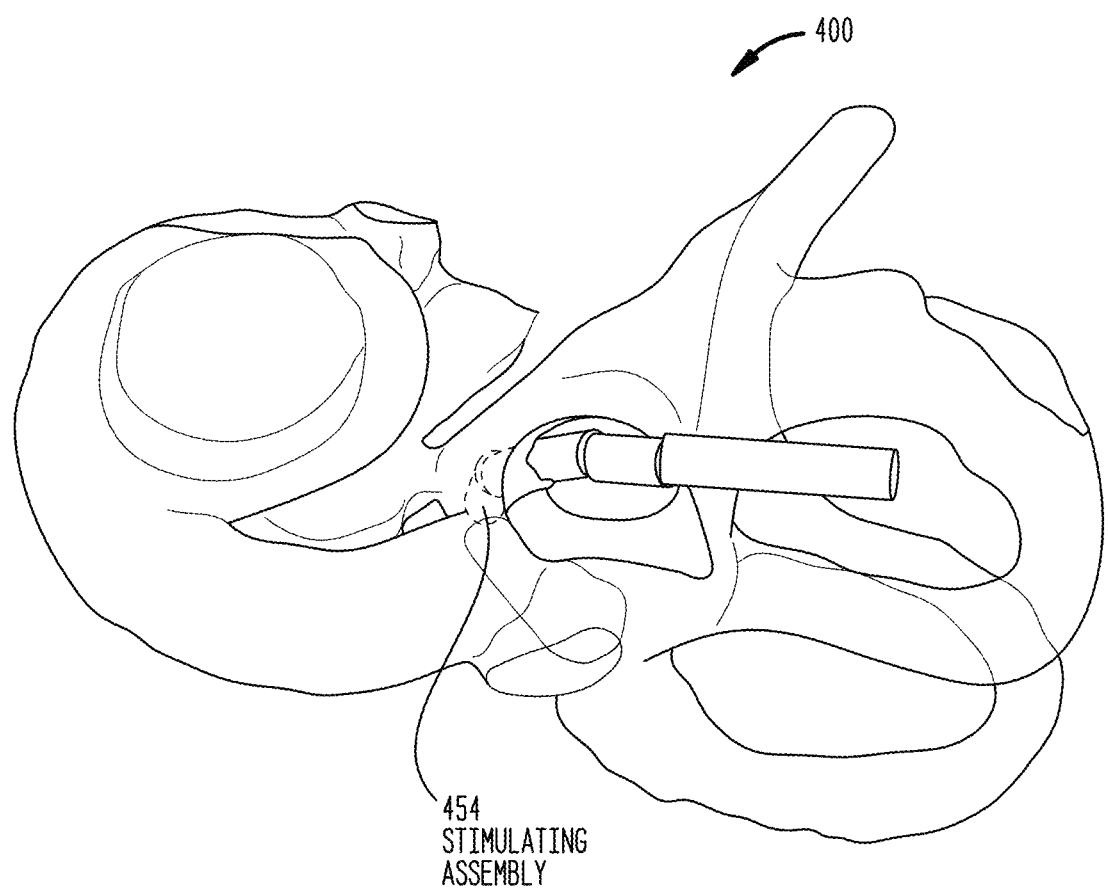
FIG. 4 is a schematic three-dimensional diagram of a recipient's inner ear having a stimulating assembly implanted therein, in accordance with certain embodiments presented herein.

FIG. 4 is a schematic three-dimensional diagram of a recipient's inner ear 400. FIG. 4 also illustrates the general location of a stimulating assembly 454 implanted in the inner ear 400 in accordance with embodiments presented herein. In FIG. 4, the stimulating assembly 454 is positioned adjacent to the saccule so as to enable electrical stimulation of the vestibular ganglion and inferior branch of the vestibular nerve (e.g., either direct stimulation or indirect stimulation through only the saccule).

The distance between implanted electrodes and target neural fibers has an impact on effectiveness of the stimulation (e.g., in terms of the current levels required, the amount of current spread and resulting cross talk, etc.). Therefore, in accordance with certain examples presented, the implanted location of a stimulating assembly can be evaluated through the use of Vestibular Response Telemetry (VRT) obtained from the otolith organ stimulation.

As used herein, Vestibular Response Telemetry refers to a process in which the implanted stimulating assembly is used to detect electrically evoked compound action potentials (ECAPs) from the vestibular nerve. More specifically, once the stimulating assembly is implanted, at least one of the electrodes of the stimulating assembly is used to deliver electrical stimulation to the recipient. The ECAPs, if any, evoked by the electrical stimulation are recorded via one or more of the other implanted electrodes for subsequent analysis. The detection of an ECAP in response to the delivered electrical stimulation indicates that the delivering electrode is sufficient proximity to the vestibular nerve for stimulation thereof. However, if an ECAP is not detected in response to the delivered electrical stimulation, the electrode is improperly positioned (i.e., not close enough to the vestibular nerve). In such circumstances, the stimulating assembly may be re-positioned and/or re-implanted within the recipient. ECAPs may be obtained from, at attempted to obtained from, any number of the electrodes inserted in the vestibular organ. In certain embodiments, the ECAP (e.g., magnitudes) obtained from an electrode can be correlated with the effectiveness that stimulation signals delivered by that electrode will have on the vestibular nerve. Such effects can be considered during the fitting process, described below.

FIG. 5A is a graph illustrating an example ECAP 562 that may be detected using Vestibular Response Telemetry, in accordance with embodiments presented herein. Also shown in FIG. 5A, at 564, are the parameters of stimulation used to evoke the ECAP 562.

Figure 5B:
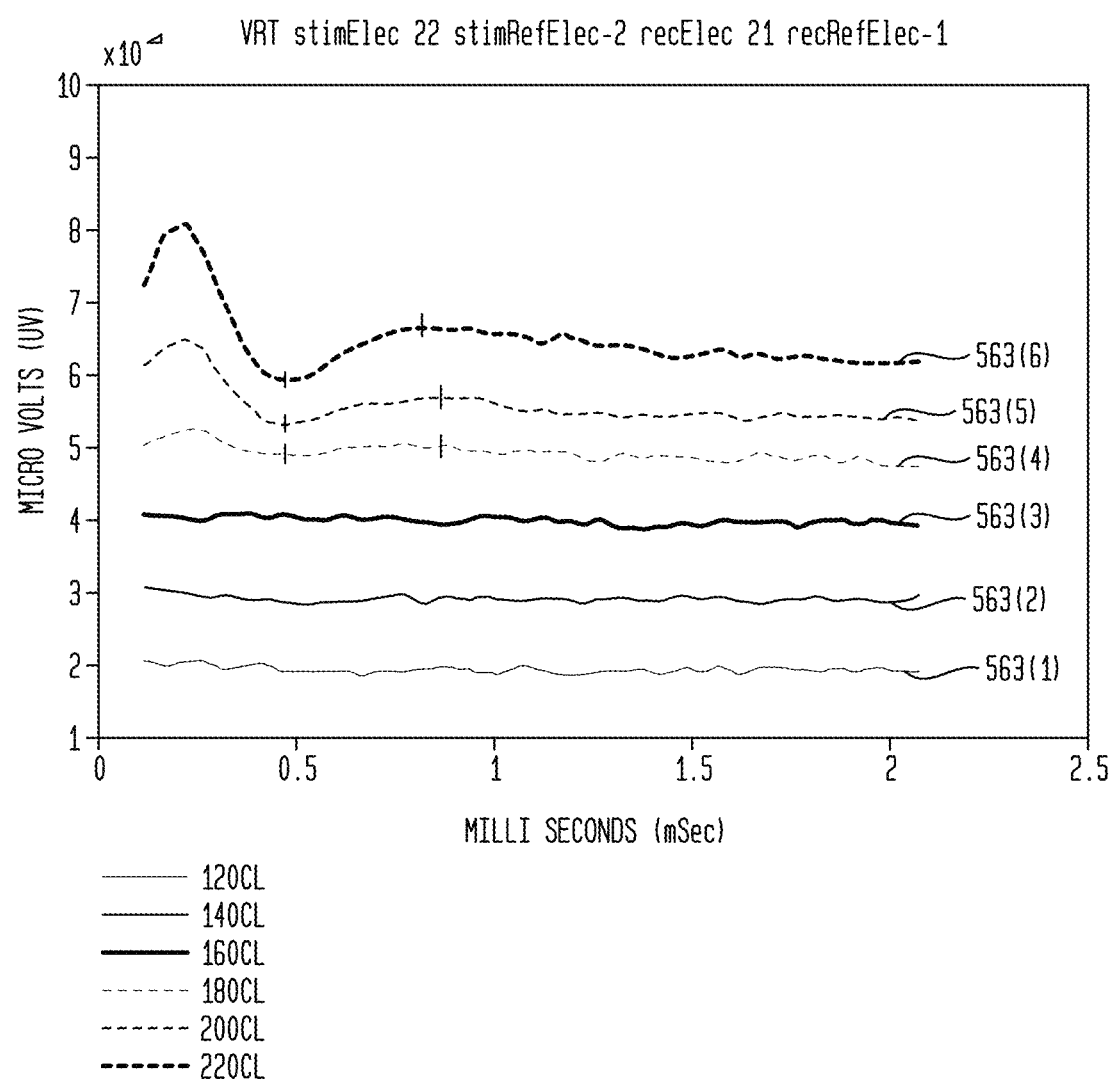
FIG. 5B is a graph illustrating ECAP magnitudes obtained from a recipient's vestibular nerve using Vestibular Response Telemetry, in accordance with certain embodiments presented herein.

In certain examples, the magnitude of a captured ECAP depend on the stimulation level used to evoke the action potential. This is shown in the graph of FIG. 5B, which is a plot of ECAP magnitude, in micro Volts ($\mu V$), versus time, in milli-seconds (mSec). As shown, FIG. 5B includes six (6) traces 563(1)-56(6) that represent the signals measured in response to stimulation at different stimulation/current levels (CLs).

Further details regarding Vestibular Response Telemetry can be found in Miguel, Angel Ramos de Miguel et al. "Vestibular Response to Electrical Stimulation of the Otolith Organs. Implications in the Development of A Vestibular Implant for the Improvement of the Sensation of Gravitoinertial Accelerations," Journal of International Advanced Otology 13(2), (2017), pgs. 154-161, the content of which is hereby incorporated by reference herein.

As noted above, the ECAPs obtained during Vestibular Response Telemetry may be used in electrode location/position optimization (e.g., to make sure the electrodes are sufficiently close to the vestibular nerve). In certain embodiments, the ECAPs obtained during Vestibular Response Telemetry may also be used in a "fitting" process. The "fitting" of a vestibular nerve stimulator to a recipient, sometimes also referred to as "programming" or "mapping." creates a set of configuration settings and other data that defines the specific operational characteristics of the vestibular nerve stimulator. In the case of vestibular nerve stimulators presented herein, fitting determines how the vestibular nerve stimulator operates to deliver electrical stimulation to the vestibular nerve to suppress erroneous balance information generated by the peripheral vestibular system (e.g., the parameters of the electrical stimulation signals prevent suppress erroneous balance information being sent to the brain of the recipient).

FIG. 6 is a flowchart illustrating an example method 670 that may be used to fit a vestibular nerve stimulator to a recipient, in accordance with embodiments presented. Merely for ease of description, method 670 of FIG. 6 will be described with reference to the vestibular nerve stimulator 132 shown in FIGS. 2A and 2B.

Method 670 begins at 672 where the electrodes 156 of vestibular nerve stimulation assembly 154, when implanted in the recipient, are used for Vestibular Response Telemetry. Again, as noted, the Vestibular Response Telemetry results can be used for electrode location optimization.

At 674, once the Vestibular Response Telemetry has been completed and ECAPs have been obtained for one or more of the electrodes 156, the minimum stimulation/current level (CL) that will generate an ECAP for one or more of the electrodes 156 is determined. The minimum current level that will generate an ECAP for an electrode is referred to as the recipient's "threshold level" for that electrode. The recipient's threshold levels may be the same or different for each of the electrodes 156.

In certain examples, the recipient's threshold level is determined for the "N" number of electrodes 156 having the highest ECAP magnitudes and/or lowest latencies (per the Vestibular Response Telemetry). In such examples, these N electrodes are the electrodes that will be used to deliver the electrical stimulation to the recipient. In one specific example, N=3 (i.e., the 3 electrodes with the highest ECAP magnitudes and/or lowest latencies are selected for use in stimulating the inferior branch of the vestibular nerve). The use of three electrodes may provide superior performance to the use of one or two electrodes (e.g., N=1 or N=2). For example, the use of three electrodes may stimulate more of the inferior branch of the vestibular nerve than the use of one or two electrodes (e.g., due to increased spread of excitation using three electrodes). If needed, non-activated electrodes 156 are deactivated by setting the current level to zero.

It is to be appreciated that operations described above with reference to 672 and 674 are optional. That is, the use of Vestibular Response Telemetry to obtain ECAPs and to determine the recipient's threshold level based thereon, may be beneficial in identifying current levels for use at the beginning of the fitting process, which may shorten the fitting process. However, the beginning current levels can also be estimated, although such estimation may lead to a longer fitting session.

Returning to the example of FIG. 6, at 676 initial vestibular stimulation parameters (i.e., initial settings for the chronic vestibular stimulation program) are selected/set for the recipient. As used herein, the vestibular stimulation parameters define the programmable attributes of the electrical stimulation signals (pulse trains) to be delivered to the recipient's vestibular nerve to suppress erroneous balance information generated by the peripheral vestibular system. As described further below, the electrical stimulation signals delivered to the vestibular nerve comprise one or more continuous pulse trains defined in terms of (i.e., generated in accordance with) vestibular stimulation parameters. The vestibular stimulation parameters may include, for example, the current level (amplitude) of the stimulation pulses delivered to the inferior branch of the vestibular nerve, the pulse rate, the pulse gap, etc. The pulse trains delivered to the vestibular nerve are referred to as "continuous" pulse trains because the stimulation parameters (e.g., rate, amplitudes, etc.) are predetermined based on subjective assessment(s) of the recipient's disbalance, and do not change/adjust based on any sensors inputs. As described further below, the vestibular stimulation parameters may be the same or different for each of the different pulse trains delivered via the different activated (e.g., N) electrodes.

After the initial vestibular stimulation parameters are set, at 678 the vestibular nerve stimulator 132 is activated (i.e., turned on) and the vestibular nerve stimulator 132 is used to stimulate the inferior branch of the recipient's vestibular nerve. At 678, the vestibular stimulation is delivered in accordance with the "current" (currently instantiated) vestibular stimulation parameters, which initially comprise the initial vestibular stimulation parameters. For delivery of the vestibular stimulation, the recipient is asked to stand with both feet together. The recipient is also asked to look forward and to keep her arms to the side touching her legs.

At 680, while the vestibular stimulation is delivered to the recipient, a determination is made as whether the current vestibular stimulation parameters are optimal to correct the recipient's disbalance problems. This determination is a subjective assessment(s) of the recipient's disbalance based on recipient feedback (e.g., asking the recipient about her feeling of balance) and the recipient's body position (i.e., whether she exhibits signs of disbalance, such as shaking, looking towards the floor, lifting her arms/imbalance, etc.). In general, the recipient is assessed for whether she exhibits a balanced position or posture (e.g., she is able to stand with her feet together, without shaking and while looking forward) and/or whether she personally feels balanced.

If it is determined at 680 that the current vestibular stimulation parameters are non-optimal (e.g., the recipient does not exhibit a balanced posture and/or does not feel balanced), then method 670) proceeds to 682. At 682, the vestibular stimulation parameters are adjusted. For example, the current level of stimulation signals delivered via one or more of the electrodes may be increased (e.g., +2), the pulse rate could be changed, etc. Once selected, the adjusted vestibular stimulation parameters are instantiated in the vestibular nerve stimulator 132 and become the "current" vestibular stimulation parameters.

After selection and instantiation of the adjusted vestibular stimulation parameters as the current vestibular stimulation parameters, method 670) returns to 678 where the adjusted vestibular stimulation parameters are used to stimulate the inferior branch of the recipient's vestibular nerve. The operations at 680, 682, and 678 are then iteratively repeated until a determination is made at 680 that the current vestibular stimulation parameters are optimal for the recipient (e.g., the recipient exhibits a balanced posture and/or feels balanced).

Once it is determined at 680 that the current vestibular stimulation parameters are optimal, the method 670) proceeds to 684. At 684, while the vestibular stimulation is delivered to the recipient, a determination is made as whether the current vestibular stimulation parameters have resulted in a loss of benefit for the recipient. This determination again is a subjective assessment based on recipient feedback, whether she exhibits signs of disbalance, and/or whether she exhibits a stimulation side-effect, such as facial nerve stimulation.

If it is determined at 684 that the current vestibular stimulation parameters have not resulted in a loss of benefit for the recipient, then method 670 end at 688. However, if some loss of benefit is observed, then the vestibular stimulation parameters are again adjusted at 686. The operations at 686 may include adjusting the vestibular stimulation parameters to a set of parameters previously assessed at 680 and determined to have the most optimal results for the recipient. The method then ends at 688.

In alternative embodiments, 686 may be omitted and, if some loss of benefit is observed at 684, the method 670 may again return to 682 for continued evaluation as described above.

As noted above, the use of Vestibular Response Telemetry to obtain ECAPs, and determining the recipient's threshold level based thereon, may be beneficial for fitting speeds up the fitting process (i.e., the threshold levels provide a good starting point for the fitting procedure, which means the time taken for the fitting process will be much shorter). However, also as noted, the use of Vestibular Response Telemetry during fitting is optional and the fitting may instead being some estimated current levels.

As noted above, the ECAP (e.g., magnitudes) obtained from an electrode can be correlated with the effectiveness that stimulation signals delivered by that electrode will have on the vestibular nerve. These effects can be considered during the fitting process of FIG. 6. For example, no ECAP is obtained from an implanted electrode (or the obtain ECAP is very low), then that electrode may be excluded from use in delivering stimulation signals to the vestibular nerve, the levels of the stimulation signals delivered from that electrode may be reduced, etc.

As noted above, a vestibular nerve stimulator in accordance with embodiments presented herein is fit to a recipient such that, once implanted, the vestibular nerve stimulator will electrically stimulate the inferior branch of the vestibular nerve in a manner that improves the recipient's sense of gravitational balance by masking vestibular noise generated by the peripheral vestibular system (e.g., suppresses, inhibits, or otherwise prevents erroneous balance information from being sent to the brain of the recipient). As noted, the electrical stimulation signals delivered to the vestibular nerve comprise one or more continuous pulse trains having predetermined and fixed stimulation parameters (e.g., amplitude/current level, frequency, pulse rate, pulse gap, etc. determined based on one or more subjective assessment(s) of the recipient's disbalance, and do not change/adjust based on any sensors inputs). As such, the fitting process is used to determine the stimulation parameters for the continuous pulse train(s) used to stimulate the vestibular nerve.

Figure 7:
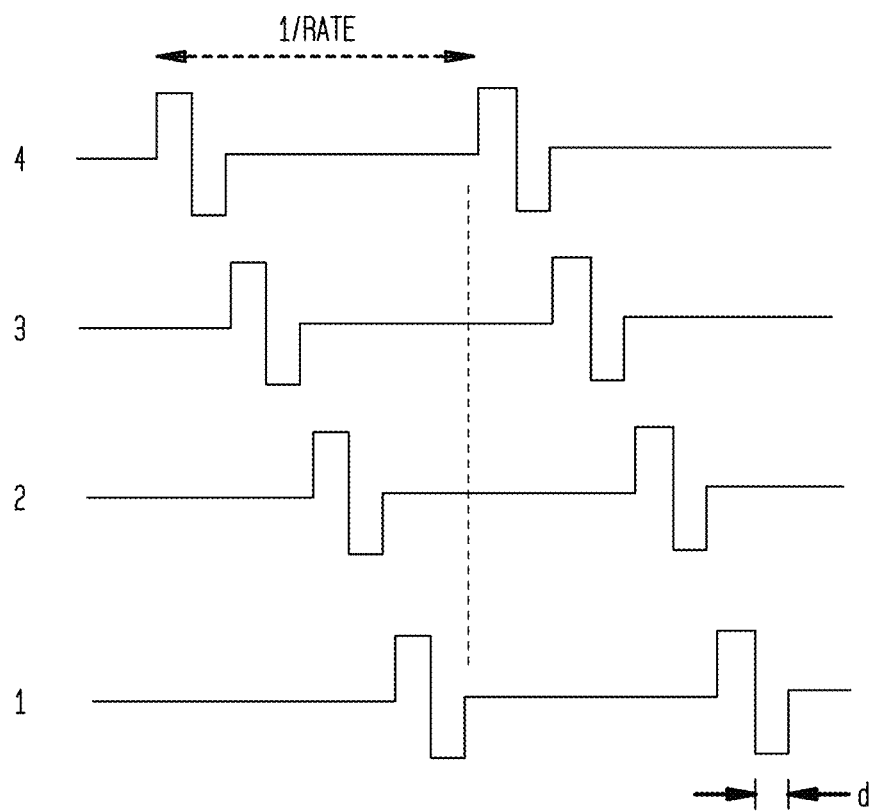
FIG. 7 illustrates portions of pulse trains that may be delivered to a recipient's vestibular nerve, in accordance with certain embodiments presented herein.

FIG. 7 illustrates portions of example continuous pulse trains that may be delivered to a recipient's vestibular nerve, in accordance with certain embodiments presented herein. In the example of FIG. 7, the pulse rate is 900 Hertz (Hz) (i.e., 1/rate equals 900 pulses per second) and the pulse gap (d) is 25 microseconds. The dynamic range may be between 1 current level (CL) and 170 CL, for example. These specific stimulation parameters are merely illustrative and, as noted, the fitting process is used to define, for example, a stimulation rate, current level, etc. that improves the recipient's balance. For example, the pulse could alternatively be set between approximately 500 Hz and approximately 5000 Hz (e.g., at approximately 1200 Hz). The stimulation parameters are determined on the subjective assessment (e.g., recipient's balance feelings, the recipient's body observed body position, etc.).

As noted, a vestibular nerve stimulator in accordance with embodiments presented generally includes a plurality of electrodes (e.g., three electrodes) implanted in the inner ear. One or all of the plurality of electrodes may be used to deliver continuous pulse trains to the recipient and the continuous pulse trains may be the same or different for different electrodes. For example, multiple electrodes may deliver pulse trains that are generated using the same fixed stimulation parameters. Alternatively, a vestibular nerve stimulator may deliver at least a first continuous pulse train to a first one of the plurality of electrodes and deliver at least a second continuous pulse train to a second one of the plurality of electrodes, where the first and second pulse trains are generated in accordance with different stimulation parameters (e.g., different current levels, different pulse rates, etc.). Again, the different stimulation parameters for the different pulse trains are determined during the fitting process, where the differences may be based on the electrode positioning. ECAP responses, subjective recipient feedback, etc.

As noted above, the vestibular nerve stimulator is configured to restore the recipient's normal sense of balance by applying electrical stimulation signals (continuous pulse trains) to the vestibular nerve for extended periods of time. In other words, a vestibular nerve stimulator electrically stimulates the recipient's vestibular nerve (e.g., the inferior branch of the vestibular nerve and/or the vestibular ganglion) in a manner (e.g., timing, stimulation parameters, etc.) that improves the recipient's sense of gravitational balance by masking of vestibular noise that would otherwise be sent to the brain by the vestibular nerve (i.e., restore the recipient's feeling of gravity to prevent them from falling). As described elsewhere herein, in certain embodiments the electrical stimulation signals are generated and delivered independent of any sensor inputs relating to motion of the head of the recipient (i.e., independent of and without correlation to angular orientation or acceleration of the head of the recipient).

As described elsewhere herein, vestibular nerve stimulators in accordance with embodiments presented herein are configured to treat "chronic" balance problems. As a result, in accordance with embodiments presented herein, the electrical stimulation signals are delivered so that the recipient continually experiences a sense of balance throughout the day and/or while performing certain activities. To ensure that the recipient continually experiences a sense of balance, electrical stimulation signals in accordance with embodiments presented herein are generally delivered for extended period of time to account for the recipient's disbalance in some manner, while taking into account recipient-specific characteristics and the residual effects of the stimulation. In certain examples, the electrical stimulation signals are delivered to the recipient continually constantly through the day (e.g., continually deliver stimulation signals for 8 hours, 12 hours, 14 hours, etc.).

For certain recipients, the vestibular nerve stimulation may produce residual effects for some period of time after cessation of the stimulation. That is, even after the vestibular nerve stimulation is terminated, certain recipient's may continue to feel "balanced" for some period of time (i.e., feel the effects of the stimulation, although no stimulation is being delivered). These residual effects may be leveraged in certain embodiments to implement periodic stimulation patterns.

For example, a vestibular nerve stimulator in accordance with embodiments presented herein could deliver stimulation signals to the vestibular nerve at a specific duty cycle over the course of the day or use of the device. In one example, a vestibular nerve stimulator could operate at a fifty (50) percent duty cycle (e.g., continuously deliver stimulation signals for 30 minutes, followed by no stimulation for the following 30 minutes), a forty (40) percent duty cycle (e.g., continuously deliver stimulation signals for 24 minutes, followed by no stimulation for the following 36 minutes), a sixty (60) percent duty cycle (e.g., continuously deliver stimulation signals for 36 minutes, followed by no stimulation for the following 24 minutes), and so on. The use of such duty cycles may be possible due to residual effects of the stimulation signals in the vestibular nerve for some period of time after cessation of the stimulation.

The residual effects of vestibular nerve stimulation may be different for different recipients, thus the selected duty cycles may be different for different recipients (e.g., recipient-specific) and could be determined during the fitting process (e.g., based on subjective assessment(s) of the recipient's disbalance). However, as noted above, vestibular nerve stimulators in accordance with embodiments presented herein are configured to treat chronic balance problems and, accordingly, electrical stimulation signals so that the recipient continually experiences a sense of balance throughout the day and/or while performing certain activities. Therefore, the duty cycles are selected so that the stimulator will deliver stimulation signals before the residual effects of prior stimulation cease. For example, if a recipient's residual effects last 60 minutes, the vestibular nerve stimulation may use a duty cycle where the device only pauses stimulation for 45 minutes. Therefore, the selected duty cycles (i.e., pauses in stimulation) are based on the recipient-specific information, such as their personal residual effects to vestibular nerve stimulation.

FIG. 8 is a flowchart of a method 890 in accordance with embodiments presented herein. Method 890 begins at 892 where a plurality of electrodes of a vestibular nerve stimulator are implanted within an inner ear of a recipient, adjacent to otolith organs of the inner ear. The inner ear of the recipient includes a peripheral vestibular system. At 894, the vestibular nerve stimulator generates electrical stimulation signals that are configured to improve the recipient's sense of gravitational balance by masking vestibular noise generated by the peripheral vestibular system. At 896, the vestibular nerve stimulator delivers, via one or more of the plurality of electrodes, the electrical stimulation signals to the inferior branch of the vestibular nerve through the otolith organs.

Vestibular nerve stimulators in accordance with embodiments presented herein are, in general, configured to treat recipients with chronic balance disorders. For example, vestibular nerve stimulators in accordance with embodiments presented herein may be used to treat bilateral vestibular hypofunction (BVH) and/or other bilateral or unilateral chronic balance disorders, that may produce: postural imbalance, unsteadiness of gait, movement-induced blurred vision or oscillopsia during walking or quick head/body movements, and/or worsening of postural imbalance or unsteadiness of gait in darkness and/or on uneven ground.

In certain embodiments, a vestibular nerve stimulator may be used to treat a recipient's vertigo. In one example method, a plurality of electrodes are implanted within an inner ear of a recipient adjacent to otolith organs of the inner ear. Electrical stimulation signals are generated and then delivered, via one or more of the plurality of electrodes, to at least the inferior branch of the vestibular nerve through one or more of the otolith organs. The electrical stimulation signals having stimulation parameters (e.g., amplitude, frequency, pulse rate, etc.) configured to mask vertigo symptoms experienced by the recipient (e.g., the stimulation signals having stimulation parameters that improve the recipient's sense of gravitational balance).

However, it is to be appreciated that the delivery of continuous pulse trains to the inferior branch of the recipient's vestibular nerve and/or vestibular ganglion, as presented herein, may also treat other types of balance disorders, such as those manifesting in balance attacks, such as Meniere's disease.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   generating electrical stimulation signals; and
   delivering the electrical stimulation signals to at least an inferior branch of a vestibular nerve of an inner ear of a recipient through one or more of otolith organs of the inner ear,
   wherein the otolith organs comprise the saccule and the utricle, and wherein the electrical stimulation signals are delivered to the vestibular nerve via only the saccule.

2. The method of claim 1, wherein the electrical stimulation signals are configured to improve the recipient's sense of gravitational balance by masking vestibular noise generated by a peripheral vestibular system of the inner ear.

3. The method of claim 1, wherein the electrical stimulation signals have stimulation parameters determined based on one or more subjective assessments of the recipient's disbalance.

4. The method of claim 3, wherein delivering the electrical stimulation signals to at least an inferior branch of a vestibular nerve of an inner ear of a recipient through one or more of otolith organs of the inner ear comprises:
   delivering the electrical stimulation signals with a duty cycle selected based on the recipient's disbalance and a residual effect of the stimulation for the recipient.

5. The method of claim 3, wherein the stimulation parameters of the electrical stimulation signals that are selected based on one or more subjective assessments of the recipient's disbalance include an amplitude of the electrical stimulation signals.

6. The method of claim 3, wherein the stimulation parameters of the electrical stimulation signals that are selected based on one or more subjective assessments of the recipient's disbalance include one or more of frequency, pulse rate, pulse gap, of the electrical stimulation signals.

7. The method of claim 1, wherein delivering the electrical stimulation signals to at least the inferior branch of the vestibular nerve through the otolith organs comprises:
   delivering at least a first continuous pulse train to at least the inferior branch of the vestibular nerve; and
   delivering at least a second continuous pulse train to at least the inferior branch of the vestibular nerve.

8. The method of claim 7, wherein the first and second continuous pulse trains are generated in accordance with first and second sets of stimulation parameters, respectively, and wherein the second set of stimulation parameters is different from the first set of stimulation parameters.

9. The method of claim 1, wherein delivering the electrical stimulation signals to at least an inferior branch of a vestibular nerve of an inner ear of a recipient through one or more otolith organs of the inner ear comprises:
   delivering the electrical stimulation signals via a stimulating assembly comprising a one or more electrodes configured to be implanted in the recipient adjacent to the otolith organs.

10. The method of claim 1, wherein delivering the electrical stimulation signals to at least an inferior branch of a vestibular nerve of an inner ear of a recipient through one or more otolith organs of the inner ear comprises:
    delivering the electrical stimulation signals to the vestibular nerve so that the recipient continually experiences a sense of balance.

11. The method of claim 1, wherein the electrical stimulation signals are generated independent of any sensor inputs relating to linear acceleration, angular motion, or angular acceleration of the head of the recipient.

* * * * *